(12) United States Patent
Saito (10) Patent No.: US 11,179,119 B2
(45) Date of Patent: Nov. 23, 2021

(54) X-RAY FLUOROSCOPIC IMAGING APPARATUS

(71) Applicant: Shimadzu Corporation, Kyoto (JP)

(72) Inventor: Atsuo Saito, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 17/039,362

(22) Filed: Sep. 30, 2020

(65) Prior Publication Data

US 2021/0113166 A1 Apr. 22, 2021

(30) Foreign Application Priority Data

Oct. 21, 2019 (JP) .............................. JP2019-192270

(51) Int. Cl.
*A61B 6/00* (2006.01)

(52) U.S. Cl.
CPC .......... *A61B 6/4014* (2013.01); *A61B 6/4441* (2013.01); *A61B 6/4476* (2013.01); *A61B 6/487* (2013.01); *A61B 6/54* (2013.01); *A61B 6/481* (2013.01)

(58) Field of Classification Search
CPC ..... A61B 6/4014; A61B 6/4441; A61B 6/481; A61B 6/4476; A61B 6/487; A61B 6/54; A61B 34/20; A61B 90/37; A61B 2090/373; A61B 2034/2057; A61B 2034/2074; A61B 6/5258; A61B 6/482; A61B 6/035; A61B 6/0457; A61B 6/547
See application file for complete search history.

(56) References Cited

U.S. PATENT DOCUMENTS

| | | | |
|---|---|---|---|
| 2005/0195945 A1 | 9/2005 | Gotoh | |
| 2015/0238159 A1* | 8/2015 | Al Assad | A61B 6/025 378/5 |

FOREIGN PATENT DOCUMENTS

JP 2005-245814 A 9/2005

* cited by examiner

*Primary Examiner* — Don K Wong
(74) *Attorney, Agent, or Firm* — Muir Patent Law, PLLC (57) ABSTRACT

This X-ray fluoroscopic imaging apparatus includes a first arm, a second arm, and a controller. The controller is configured to move a second base to move the second arm to a position where the second arm does not interfere with the first arm when the first arm and the second arm interfere with each other and change the angle of the second arm so that the angle of the second arm becomes a predetermined imaging angle to arrange the first arm and the second arm at positions where the first arm and the second arm do not interfere with each other to perform imaging.

8 Claims, 9 Drawing Sheets

FIG.1

FIG.2A
Side View

FIG.2B
Perspective View

FIG.3A
Side View

FIG.3B
Schematic diagram viewed from the long axis direction of the top board

FIG.4

FIG.5A
Perspective view of the first imaging position (ROA+Cranial) and the sixth imaging position (LAO+Cranial)

FIG.5B
Plan view of the first imaging position (RAO+Cranial) and the sixth imaging position (LAO+Cranial)

FIG.6A
Perspective view of the second imaging position (RAO) and the seventh imaging position (LAO)

FIG.6B
Plan view of the second imaging position (RAO) and the seventh imaging position (LAO)

FIG.7A
Perspective view of the third imaging position (RAO+Caudal) and the eighth imaging position (LAO+Caudal)

FIG.7B
Plan view of the third imaging position (RAO+Caudal) and the eighth imaging position (LAO+Caudal)

FIG.8
Comparative Example

FIG.9A

Movement of Second Base

FIG.9B

Movement of First Arm

FIG. 10A
Perspective view of the fourth imaging position (Cranial) and the fifth imaging position (Caudal)

FIG. 10B
Plan view of the fourth imaging position (Cranial) and the fifth imaging position (Caudal)

FIG.11

Imaging processing at the fourth imaging position and the fifth imaging position

X-RAY FLUOROSCOPIC IMAGING APPARATUS

CROSS-REFERENCE TO RELATED APPLICATIONS

The priority application number JP2018-082499, entitled "X-ray fluoroscopic imaging apparatus", filed on Apr. 23, 2018 and invented by Atsuo Saito, and the priority application number JP2019-192270, entitled "X-ray fluoroscopic imaging apparatus", filed on Oct. 21, 2019 and invented by Atsuo Saito, upon which this patent application is based, are hereby incorporated by reference in their entirety.

BACKGROUND OF THE INVENTION

Field of the Invention

The present invention relates to an X-ray fluoroscopic imaging apparatus, and more particularly to an X-ray fluoroscopic imaging apparatus capable of performing imaging from two different directions at a time.

Description of the Background Art

Conventionally, an X-ray fluoroscopic imaging apparatus capable of performing imaging from two different directions at a time is known. Such an X-ray fluoroscopic imaging apparatus is disclosed, for example, in Japanese Unexamined Patent Application Publication No. 2005-245814.

An X-ray fluoroscopic imaging apparatus is capable of non-invasively imaging an internal structure of a subject, and is used to diagnose a disease or support a surgical operation in a medical field. For example, in an operation of a cardiovascular system, in order to grasp a position and a blood flow of a coronary artery, an X-ray fluoroscopic imaging apparatus supports the operation by imaging a subject from various angles after administering a contrast agent to the subject.

As an X-ray fluoroscopic imaging apparatus capable of imaging a subject from various angles, there is an X-ray fluoroscopic imaging apparatus disclosed in Japanese Unexamined Patent Application Publication No. 2005-245814. The X-ray fluoroscopic imaging apparatus disclosed in Japanese Unexamined Patent Application Publication No. 2005-245814 is provided with a first arm rotatably held by a base provided on a floor and a second arm rotatably held by a base provided on a ceiling. The first arm is provided with a first X-ray source and a first detector. The second arm is provided with a second X-ray source and a second detector. An X-ray fluoroscopic imaging apparatus provided with a first arm and a second arm as disclosed in Japanese Unexamined Patent Application Publication No. 2005-245814 is generally referred to as a biplane type X-ray fluoroscopic imaging apparatus.

The X-ray fluoroscopic imaging apparatus disclosed in Japanese Unexamined Patent Application Publication No. 2005-245814 is configured such that a subject can be imaged from two different directions by arranging the first arm and the second arm in different directions. By imaging the subject from various angles using such an X-ray fluoroscopic imaging apparatus after administrating a contrast agent, a physician or the like can grasp a position, a blood flow, etc., of a coronary artery of the subject.

Here, when assisting a heart operation of a subject, there are eight directions for imaging a subject. The eight directions include a combination of each of a left oblique direction, a front direction, and a right oblique direction of the subject and directions in which X-rays are obliquely irradiated to the subject from one end side or the other end side of the top board in the longitudinal cross-sectional plane along the long axis of the top board. These imaging directions are expressed by a combination of LAO (left oblique), RAO (right oblique), Cranial (one end side in the longitudinal cross-sectional plane along the long axis of the top board), and Caudal (the other end side in the longitudinal cross-sectional plane along the long axis of the top board), which are generally known imaging directions in the medical field, etc.

The biplane type X-ray fluoroscopic imaging apparatus disclosed in Japanese Unexamined Patent Application Publication No. 2005-245814 can perform imaging from different directions at a time by using the first arm and the second arm. However, in the biplane type X-ray fluoroscopic imaging apparatus as disclosed in Japanese Unexamined Patent Application Publication No. 2005-245814, it is not always possible to perform imaging from any directions by two arms, so that there is a case in which imaging can be performed by only one arm due to the interference between the arm and the base depending on the direction.

Specifically, when it is attempted to perform imaging by using two arms at a time at a Cranial (one end side of the top board in the longitudinal cross-sectional plane along a long axis of the top board) imaging position and a Caudal (the other end side of the top board in the longitudinal cross-sectional plane along the long axis of the top board) imaging position, it is considered that imaging at a time by using two arms cannot be performed due to the interference between the base of the first arm and the second arm. Therefore, in the X-ray fluoroscopic imaging apparatus disclosed in Japanese Unexamined Patent Application Publication No. 2005-245814, the imaging at the Cranial (one end side of the top board in the longitudinal cross-sectional plane along the long axis of the top board) imaging position and the Caudal (the other end side of the top board in the longitudinal cross-sectional plane along the long axis of the top board) imaging position has to be performed separately by using the first arm, which causes a problem that the number of administering a contrast agent is increased. Further, the increased number of times of administering a contrast agent causes a problem that imaging time is extended.

SUMMARY OF THE INVENTION

The present invention has been made to solve the above-described problems, and one object of the present invention is to provide an X-ray fluoroscopic imaging apparatus capable of suppressing an increase in the number of times of administering a contrast agent and capable of shortening an imaging time.

In order to achieve the above-described object, the X-ray fluoroscopic imaging apparatus according to the first aspect of the present invention includes:

a first arm configured to support a first X-ray source and a first detector;

a second arm including a second arm part and a base unit, the second arm part being held by a base and configured to support a second X-ray source and a second detector, and the base unit including a base moving mechanism for moving the base;

a second arm driving mechanism configured to drive the second arm; and a controller configured to control the second arm driving mechanism and the base moving mechanism, wherein the controller is configured such that in a case where the first arm and the second arm interfere with each other when the first arm and the second arm are moved to respective predetermined imaging angles or when the first arm and the second arm have reached the respective predetermined imaging angles, the base is moved by the base moving mechanism to move the second arm together with the base unit to a position where the second arm does not interfere with the first arm and that an angle of the second arm is changed by the second arm driving mechanism so that the second arm does not interfere with the first arm and the angle of the second arm becomes the predetermined imaging angle to arrange the first arm and the second arm at positions where the first arm and the second arm do not interfere with each other to perform imaging.

As described above, the X-ray fluoroscopic imaging apparatus according to the first aspect of the invention is provided with the controller. The controller is configured such that in a case where the first arm and the second arm interfere with each other when the first arm and the second arm are moved to respective predetermined imaging angles or when the first arm and the second arm have reached the respective predetermined imaging angles, the base is moved by the base moving mechanism to move the second arm together with the base unit to a position where the second arm does not interfere with the first arm and that an angle of the second arm is changed by the second arm driving mechanism so that the second arm does not interfere with the first arm and the angle of the second arm becomes the predetermined imaging angle to arrange the first ram and the second arm at imaging positions where the first arm and the second arm do not interfere with each other to perform imaging.

As a result, in a case where the first arm and the second arm interfere with each other when the first arm and the second arm are moved to respective predetermined imaging angles or when the first arm and the second arm have reached the respective predetermined imaging angles, since it is possible to move the second arm together with the base unit, the interference between the first arm and the second arm can be suppressed. For this reason, even in cases where imaging is performed from directions in which the first arm and the second arm interfere with each other, imaging can be performed at a time by using the first arm and the second arm. As a result, by administering a contrast agent once, imaging at a time from two directions in which the first arm and the second arm interfere with each other can be performed. Therefore, it is possible to suppress the increase in the number of times of administering a contrast agent as compared with a case in which the imaging is performed separately in two times from the directions in which the first arm and the second arm interfere with each other.

Further, for example, imaging can be performed at a time from two X-ray irradiation directions, i.e., the direction facing the front of the subject and the direction oblique to the subject from one end side or the other end side of the top board for placing the subject thereon in a longitudinal cross-section plane along the long axis of the board. As a result, as compared with the cases in which the imaging is performed separately from a front of the subject and from one end side or the other end side of the top board in the longitudinal cross-sectional plane along the long axis of the top board, the number of times of imaging can be reduced, which in turn can reduce the imaging time. As described above, in the present invention, the X-ray fluoroscopic imaging apparatus can suppress the increase in the number of times of administering a contrast agent and can shorten the imaging time.

In the X-ray fluoroscopic imaging apparatus according to the first aspect of the invention, preferably, the base moving mechanism includes a first rotation axis provided on a floor and a second rotation axis provided at a position away from the first rotation axis, and the controller is configured to rotate the base unit by the base moving mechanism to rotate the second arm so that the second arm is arranged at a position where the second arm does not interfere with the first arm. With this configuration, since the first rotation axis and the second rotation axis are provided at positions away from each other, by rotating the base unit, it is possible to easily change the position of the second arm. Consequently, by rotating the base unit, it is possible to easily arrange the second arm in a position where the second arm does not interfere with the first arm.

In this case, preferably, it is configured such that the first rotation axis and the second rotation axis are each a rotation axis oriented in a vertical direction with respect to the floor, and the controller is configured to rotate the base unit by the base moving mechanism to arrange the second rotation axis on a long side of a top board for placing a subject thereon. With this configuration, since it becomes possible to arrange the second rotation axis on the long side of the top board, when the first arm moves to the short side of the top board, it is possible to suppress that a part of the first arm and the second arm interfere with each other. Consequently, it is possible to more assuredly suppress that a part of the second arm interferes with the first arm.

In the configuration in which the second arm is arranged at a position where the second arm does not interfere with the first arm by rotating the base unit to rotate the second arm, preferably, the second arm further includes a detector rotation mechanism for rotating the second detector, and the controller is configured to rotate the second detector by the detector rotation mechanism by an angle corresponding to a rotation angle of the second arm so as not to change an orientation of a subject in an X-ray image to be acquired due to rotation of the second arm by the base moving mechanism.

With this configuration, by rotating the second detector in accordance with the rotation angle of the second arm, even in cases where the second arm is arranged at a position where the second arm does not interfere with the first arm when imaging the subject is performed by using the second arm from the desired imaging angle, it is possible to acquire the same X-ray image as an X-ray image captured by imaging without rotating the subject. Therefore, when imaging a subject from a desired imaging angle, it is possible to perform imaging so that the orientation of the subject to be reflected in an X-ray image is also oriented in the desired direction. As a result, the user usability can be improved.

In the X-ray fluoroscopic imaging apparatus according to the first aspect above, preferably, the controller is configured to arrange the first arm and the second arm at positions where X-rays are emitted to the subject in oblique directions from one end side and the other end side of the top board in a longitudinal cross-sectional plane along a long axis of the top board to perform imaging.

With this configuration, even in the case of imaging a subject from two different directions, i.e., a direction from one end side of the long axis of the top board and a direction from the other end side thereof, it is possible to suppress that the first arm and the second arm interfere with each other. Consequently, it is possible to perform imaging from two different directions, i.e., a direction from one end side of the top board and a direction from the other end side thereof, by one imaging operation.

In the X-ray fluoroscopic imaging apparatus according to the first aspect above, preferably, the X-ray fluoroscopic imaging apparatus further includes a first arm driving mechanism configured to drive the first arm. The controller is configured to move the base unit by the base moving mechanism from a short side of the top board for placing a subject thereon to a long side thereof in a plan view and arrange the first arm by the first arm driving mechanism on the short side of the top board so that the second arm is arranged at a position where the second arm does not interfere with the first arm.

With this configuration, after moving the base unit from the short side of the top board to the long side thereof, it is possible to arrange the first arm on the short side of the top board. Consequently, even when the second arm is arranged at a position where the second arm interferes with the first arm, it is possible to move the first arm after moving the second arm, which can assuredly suppress the second arm from interfering with the first arm.

In the X-ray fluoroscopic imaging apparatus according to the first aspect above, preferably, the controller is configured to arrange the first arm and the second arm at mutually different four relative positions to image a subject from eight directions in which a short axis direction of the top board in a horizontal plane along a long axis of the top board for placing a subject thereon and directions in which X-rays are obliquely emitted to a subject from one end side or the other end side of the top board in a longitudinal cross-sectional plane along the long axis of the top board are combined.

With this configuration, it is possible to perform imaging from eight directions by arranging the first arm and the second arm at four relative positions. As a result, as compared with the case in which a subject is imaged separately by changing a direction in which X-rays are obliquely emitted to the subject from one end side of the top board or the other end side thereof in the longitudinal cross-section along the long axis of the top board, the number of times of imaging can be reduced. This in turn can suppress the increase in the number of times of administering a contrast agent.

An X-ray fluoroscopic imaging apparatus according to a second aspect of this invention, includes:
  an imaging unit including a first arm and a second arm, the imaging unit being capable of imaging a subject from different directions; and
  a controller configured to control the imaging unit,
  wherein the controller is configured to perform imaging from eight directions in which each of a right oblique direction, a front direction, and a left oblique direction of the subject and directions in which X-rays are obliquely emitted to the subject from one end side or the other end side of a top board for placing a subject thereon in a longitudinal cross-sectional plane along a long axis of the top board are combined, and
  wherein in a case in which the first arm and the second arm interfere with each other when the first arm and the second arm are moved to respective predetermined imaging angles or when the first arm and the second arm have reached the respective predetermined imaging angles at a time of imaging the subject in directions in which the front direction of the subject and directions in which X-rays are emitted to the subject from one end side or the other end side of the top board are combined, between eight directions, the controller is configured to rotate a base unit of the second arm to rotate the second arm together with the base unit and change an angle of the second arm so that the second arm does not interfere with the first arm and the angle of the second arm becomes a predetermined imaging angle to arrange the first arm and the second arm at mutually non-interference positions to perform imaging.

In the X-ray fluoroscopic imaging apparatus according to the second aspect of this invention, as described above, the X-ray fluoroscopic imaging apparatus is provided with the controller configured to rotate a base unit of the second arm to rotate the second arm together with the base unit and change an angle of the second arm so that the second arm does not interfere with the first arm and the angle of the second arm becomes a predetermined imaging angle to arrange the first arm and the second arm at mutually non-interference positions to perform imaging.

With this, in the same manner as in the above-described first aspect of the present invention, it is possible to perform imaging at a time from two directions in which the first arm and the second arm interfere with each other. Therefore, by performing imaging four times in two directions, imaging in eight directions can be performed, so that it is possible to suppress the increase in the number of times of administering a contrast agent. Furthermore, by performing imaging four times in two directions, it is possible to perform imaging in eight directions. Therefore, as compared with the case in which imaging is performed separately from the front of the subject and one end side of the top board or the other end side thereof in the longitudinal cross-sectional plane along the long axis of the top board, the number of imaging can be reduced, so that the imaging time can be shortened. As described above, the present invention can provide an X-ray fluoroscopic imaging apparatus capable of suppressing an increase in the number of times of administering a contrast agent and shortening the imaging time.

According to the present invention, as described above, it is possible to provide an X-ray fluoroscopic imaging apparatus capable of suppressing an increase in the number of times of administering a contrast agent and shortening the imaging time.

DESCRIPTION OF THE PREFERRED EMBODIMENT

Hereinafter, embodiments in which the present invention is embodied will be described with reference to the attached drawings.

Referring to FIG. 1 to FIG. 10, the configuration of an X-ray fluoroscopic imaging apparatus 100 according to an embodiment of the present invention will be described.

Configuration of X-Ray Fluoroscopic Imaging Apparatus

First, referring to FIG. 1, the configuration of the X-ray fluoroscopic imaging apparatus 100 according to one embodiment of the present invention will be described.

Figure 1:
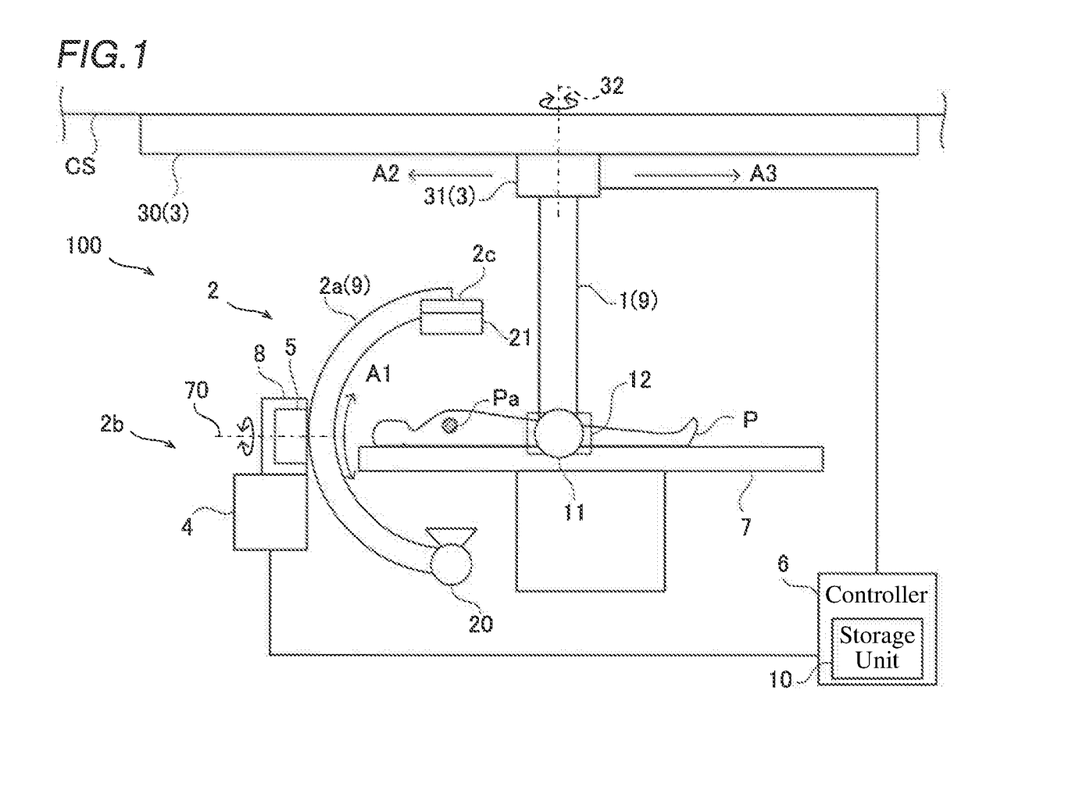
FIG. 1 is a schematic diagram showing the entire configuration of an X-ray fluoroscopic imaging apparatus according to one embodiment of the present invention.

As shown in FIG. 1, the X-ray fluoroscopic imaging apparatus 100 is provided with a first arm 1, a second arm 2, a first arm driving mechanism 3, a base moving mechanism 4, a second arm driving mechanism 5, and a controller 6. In this embodiment, the first arm 1 and the second arm 2 are each configured as an imaging unit 9 capable of imaging a subject P placed on a top board 7 from mutually different directions. The X-ray fluoroscopic imaging apparatus 100 is a so-called biplane type X-ray fluoroscopic imaging apparatus equipped with the first arm 1 and the second arm 2. In this embodiment, the X-ray fluoroscopic imaging apparatus 100 is installed in an examination room and is configured to image the subject in a state in which a contrast agent is administered to the subject P, so that a doctor or the like performs treatments, diagnostics, etc., of the region of interest of the subject P. The example shown in FIG. 1 is an example in which the X-ray fluoroscopic imaging apparatus 100 performs imaging of a heart Pa of a subject P to thereby support a doctor or the like.

The first arm 1 has an arc-shape with one end and the other end supporting a first X-ray source 11 and a first detector 12, respectively. The first arm 1 is a so-called C-shaped arm. The first arm 1 is held by a first arm driving mechanism 3 mounted on a ceiling CS of an examination room. In the example shown in FIG. 1, the first arm 1 is arranged so that the long sides of the top board 7 are positioned between the first X-ray source 11 and the first detector 12.

The first arm driving mechanism 3 is mounted on the ceiling CS of the examination room, and includes a linear motion mechanism 30 and a first base 31. The linear motion mechanism 30 is configured to move the first arm 1 together with the first base 31 in the long axis direction of the top board 7 (in the arrow A2 direction and the arrow A3 direction). The linear motion mechanism 30 includes, for example, a ball screw or a linear motor.

The first base 31 holds the first arm 1 rotatably about the first rotation axis 32. Further, the first base 31 is configured to move the first arm 1 in the circumferential direction of the first arm 1. The first base 31 includes, for example, a motor and the like.

The first X-ray source 11 is configured to generate X-rays when a high voltage is applied based on a signal from the controller 6 and emit the generated X-rays toward the first detector 12. The first detector 12 is configured to detect X-rays, convert the detected X-rays to electric signals, and read the converted electric signals as image signals. The first detector 12 is, for example, a Flat Panel Detector.

The second arm 2 includes a second arm part 2a, a base unit 2b, and a detector rotation mechanism 2c. The base unit 2b includes a base moving mechanism 4 for moving a second base 8. The second arm part 2a has an arc-shape, one end and the other end supporting the second X-ray source 20 and the second detector 21, respectively. The second arm 2 is a so-called C-shaped arm. The second arm part 2a is rotatably held by the second base 8. In the example shown in FIG. 1, the second arm 2 is arranged such that the short side of the top board 7 is positioned between the second X-ray source 20 and the second detector 21, The second X-ray source 20 and the second detector 21 have the same configurations as the first X-ray source 11 and the first detector 12, respectively. The second detector 21 is configured to detect the X-rays emitted from the second X-ray source 20, convert the detected X-rays to electric signals, and read the converted electric signals as image signals.

The second base 8 holds the second arm part 2a. The second base 8 includes, for example, a motor. Note that the second base 8 is an example of the "base" recited in claims.

The base moving mechanism 4 is configured to move the second base 8 to thereby move the second arm 2 together with the second base 8 to the desired imaging position. In this embodiment, the base moving mechanism 4 is configured to move the second base 8 to thereby move the second arm 2 together with the second base 8 to a position where the second arm 2 does not interfere with the first arm 1. The detailed configuration of the base moving mechanism 4 will be described later.

The detector rotation mechanism 2c is provided on the second arm part 2a, and is configured to rotate the second detector 21. Specifically, the detector rotation mechanism 2c is configured to rotate the second detector 21 in the rotation direction about the axis 23 (see FIG. 5A) connecting the second X-ray source 20 and the second detector 21.

The second arm driving mechanism 5 is configured to drive the second arm part 2a. Specifically, the second arm driving mechanism 5 is configured to rotate the second arm part 2a about the second rotation axis 70. Further, the second arm driving mechanism 5 is configured to move the second arm part 2a in the circumferential direction (direction of the arrow A1) of the second arm part 2a.

The controller 6 is configured to control the first arm driving mechanism 3, the base moving mechanism 4, the second arm driving mechanism 5, and the second base 8. Specifically, the controller 6 is configured to control such that the first arm 1 and the second arm 2 are arranged at predetermined positions by the first arm driving mechanism 3, the base moving mechanism 4, the second arm driving mechanism 5, and the second base 8 to perform imaging. The controller 6 includes, for example, a CPU (Central Processing Unit). The detailed configuration in which the controller 6 moves the second base 8, the first arm 1, and the second arm 2 will be described later.

The controller 6 includes a storage unit 10. The storage unit 10 is configured to store positions, etc., for arranging the first arm 1 and the second arm 2 when imaging at each imaging position. The storage unit 10 includes, for example, an HDD (Hard Disk Drive) and a nonvolatile memory.

The imaging unit 9 includes the first arm 1 and the second arm 2 and is configured to perform imaging from any direction in which each of a right oblique direction (RAO) (see FIG. 3B), a front direction, and a left oblique direction (LAO) (see FIG. 3B) of the subject P and directions in which X-rays are obliquely emitted to the subject P from one end side (Cranial) (see FIG. 3A) or the other end side (Caudal) (see FIG. 3A) of the top board 7 for placing a subject P thereon in a longitudinal cross-sectional plane along the long axis of the top board 7 are combined based on the input signals from the controller 6. In this embodiment, the imaging unit 9 is configured to perform imaging from eight directions in which RAO, front, and LAO, and Cranial, front, and Caudal are combined. The detailed explanation of directions for emitting X-rays to the subject P and imaging positions will be described later.

Configuring Base Moving Mechanism

Figure 2A:
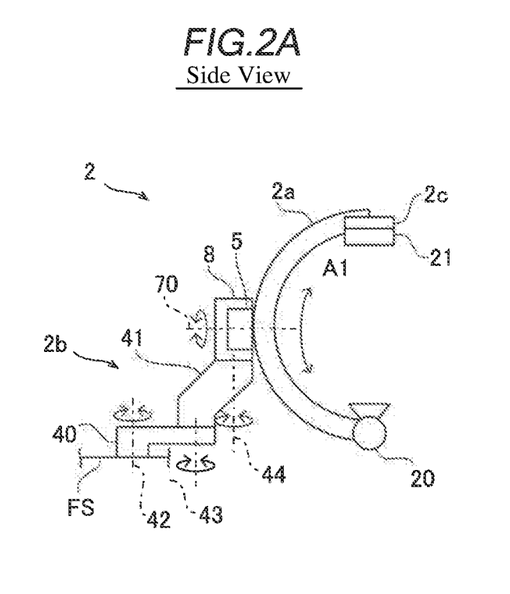
FIG. 2A is a side view for explaining the configuration of a base unit and a base moving mechanism according to one embodiment of the present invention.
Figure 2B:
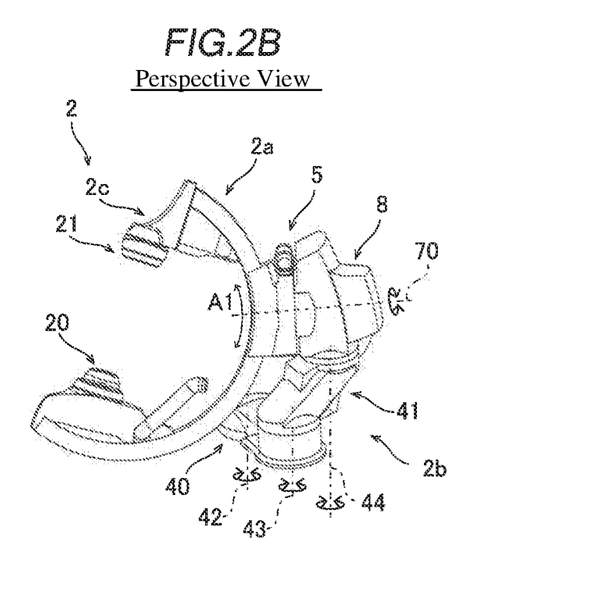
FIG. 2B is a perspective view for explaining the configuration of the base unit and the base moving mechanism according to one embodiment of the present invention.

Next, referring to FIG. 2, the configuration of the base moving mechanism 4 in this embodiment will be described. FIG. 2A is a side view of the second arm 2, the second base 8, and the base moving mechanism 4. FIG. 2B is a perspective view of the second arm 2, the second base 8, and the base moving mechanism 4.

As shown in FIG. 2, the base moving mechanism 4 includes a first rotation unit 40 provided on the floor FS and a second rotation unit 41 rotatably held by the first rotation unit 40 and rotatably holding the second base 8. The first rotation unit 40 includes a base axis 42 and an intermediate axis 43 provided on a position away from the base axis 42. The second rotation unit 41 includes a horizontal rotation axis 44.

That is, the base moving mechanism 4 includes the base axis 42 provided on the floor FS, the intermediate axis 43 provided on a position away from the base axis 42, and the horizontal rotation axis 44 provided at a position different from the base axis 42 and the intermediate axis 43. Note that the base axis 42 and the intermediate axis 43 are each a rotation axis oriented in the vertical direction with respect to the floor FS. Also note that the horizontal rotation axis 44 is a rotation axis oriented in the vertical direction with respect to the floor FS. With this, the second base 8 and the second arm part 2a can be moved horizontally to desired positions by combining the rotation about the base axis 42, the rotation about the intermediate axis 43, and the rotation about the horizontal rotation axis 44. Note that the base axis 42 and the intermediate axis 43 are examples of the "first rotation axis" and the "second rotation axis" recited in claims, respectively.

X-Ray Irradiation Directions and Imaging Positions

Next, referring to FIG. 3 and FIG. 4, X-ray irradiation directions and imaging positions in this embodiment will be described.

Figures 3A, 3B:
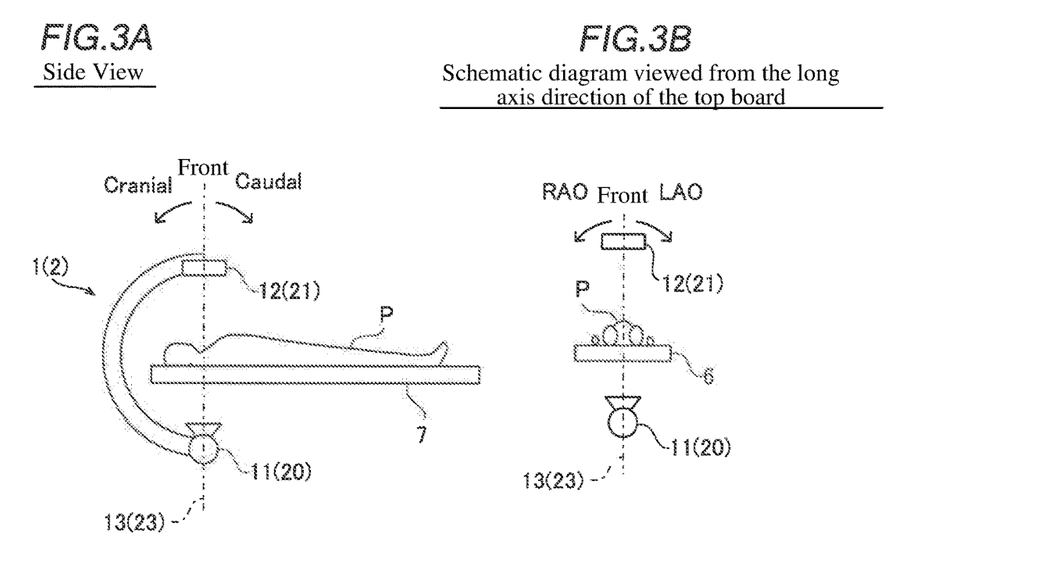
FIG. 3A is a schematic diagram for explaining imaging directions according to one embodiment of the present invention.
FIG. 3B is a schematic diagram for explaining imaging directions according to one embodiment of the present invention.

FIG. 3A shows a schematic diagram when a subject P is viewed from its side. FIG. 3B shows a schematic diagram when the subject P is viewed from a long axis of the top board 7 (from a leg-side of the subject).

As shown in FIG. 3A, the arrangement in which the first detector 12 (second detector 21) is moved on the head side of the subject P with respect to the state in which the axis 13 (23) connecting the first X-ray source 11 (second X-ray source 20) and the first detector 12 (second detector 21) is perpendicular to the top board 7 is referred to as "Cranial". Further, the arrangement in which the first detector 12 (second detector 21) is moved on the leg side of the subject P with respect to the state in which the axis 13 (23) connecting the first X-ray source 11 (second X-ray source 20) and the first detector 12 (second detector 21) is perpendicular to the top board 7 is referred to as "Caudal". Note that Cranial and Caudal are an example of the "direction in which X-rays are obliquely emitted to the subject from one end side of the top board in a longitudinal cross-sectional plane along a long axis of the top board" and an example of the "direction in which X-rays are obliquely emitted to the subject from the other end side of the top board in a longitudinal cross-sectional plane along a long axis of the top board" recited in claims, respectively.

As shown in FIG. 3B, the arrangement in which the first detector 12 (second detector 21) is moved on the right-hand side of the subject P with respect to the state in which the axis 13 (23) connecting the first X-ray source 11 (second X-ray source 20) and the first detector 12 (second detector 21) is perpendicular to the top board 7 is referred to as "RAO". Further, the arrangement in which the first detector 12 (second detector 21) is moved on the left-hand side of the subject P with respect to the state in which the axis 13 (23) connecting the first X-ray source 11 (second X-ray source 20) and the first detector 12 (second detector 21) is perpendicular to the top board 7 is referred to as "LAO". Note that RAO and LAO are an example of the "right oblique position of the subject" and the "left oblique position of the subject" recited in claims, respectively. Also note that RAO and LAO are an example of the "short axis direction in a horizontal plane along the long axis of the top board".

In this embodiment, the controller 6 is configured to arrange the first detector 12 and the second detector 21 in any of eight positions in which Cranial, Caudal, RAO, and LAO are combined.

Figure 4:
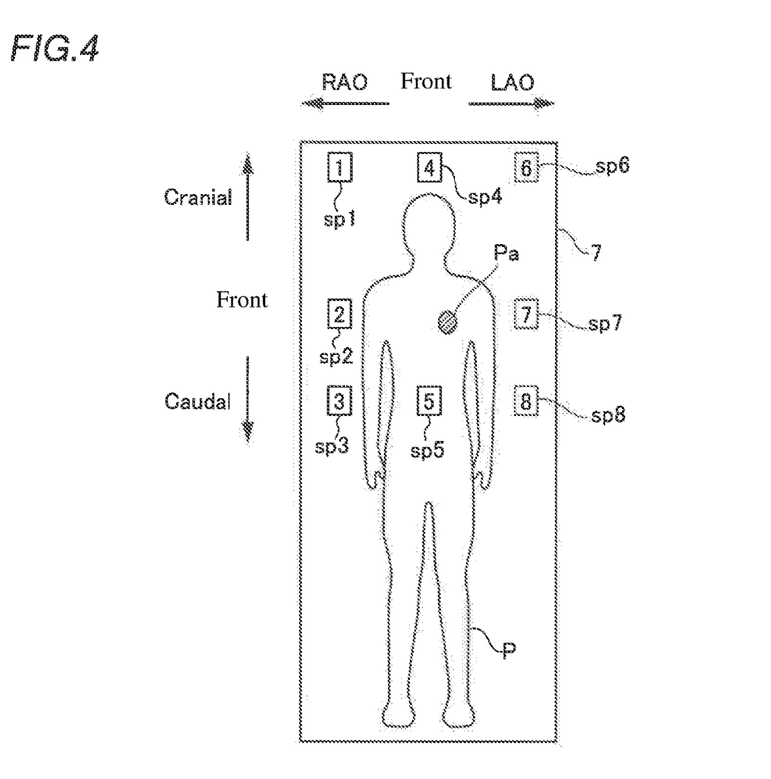
FIG. 4 is a schematic diagram for explaining positions where an X-ray fluoroscopic imaging apparatus according to one embodiment of the present invention images a subject.

FIG. 4 is a schematic diagram in which the subject P on the top board 7 is viewed from the ceiling side. In the example shown in FIG. 4, the numerals 1 to 8 enclosed in squares show the first imaging position sp1 to the eighth imaging position sp8, respectively. In this embodiment, the controller 6 is configured to arrange the first detector 12 and the second detector 21 in any of the first imaging position sp1 to the eighth imaging position sp8 shown in FIG. 4. Specifically, the controller 6 is configured to perform imaging from eight directions in which RAO and LAO, and Cranial and Caudal are combined by arranging the first arm 1 and the second arm 2 at mutually different four relative positions.

The first imaging position sp1 is an imaging position in which RAO and Cranial are combined. The second imaging position sp2 is an imaging position of RAO. The third imaging position sp3 is an imaging position in which RAO and Caudal are combined. The fourth imaging position sp4 is an imaging position of Cranial. The fifth imaging position sp5 is an imaging position of Caudal. The sixth imaging position sp6 is an imaging position in which LAO and Cranial are combined. The seventh imaging position sp7 is an imaging position of LAO. The eighth imaging position sp8 is an imaging position in which LAO and Caudal are combined.

Arrangement of First Arm and Second Arm in Each Imaging Position

Next, referring to FIG. 5 to FIG. 10, the arrangements of the first arm 1 and the second arm 2 in each imaging position will be described.

<Imaging at First Imaging Position and Sixth Imaging Position>

Figure 5A:
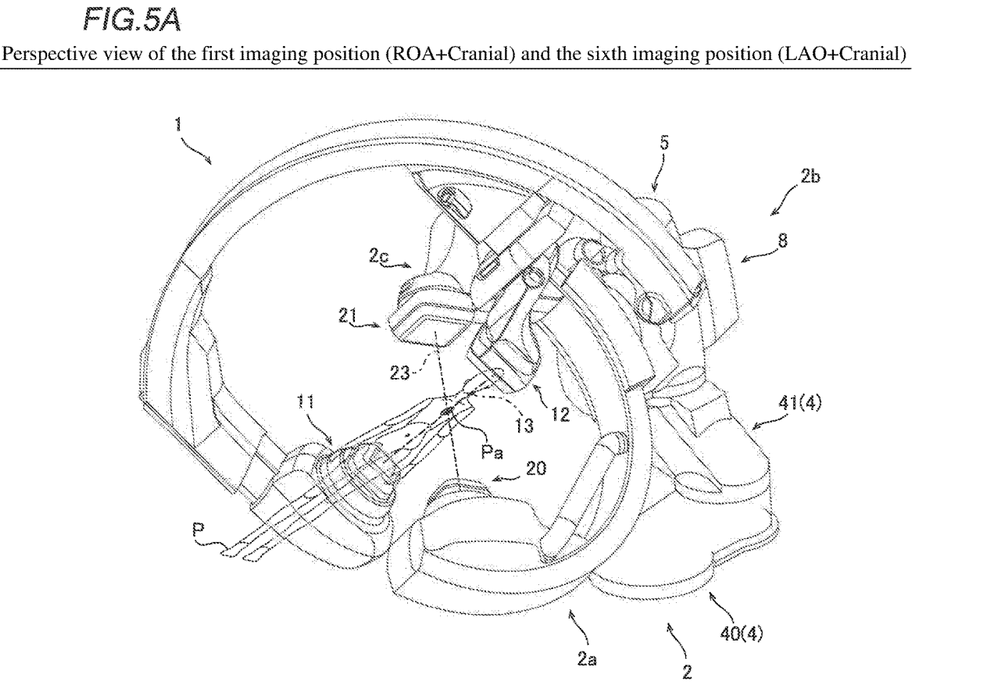
FIG. 5A is a perspective view showing the arrangements of the first arm and the second arm at a first imaging position and a sixth imaging position according to one embodiment of the present invention.
Figure 5B:
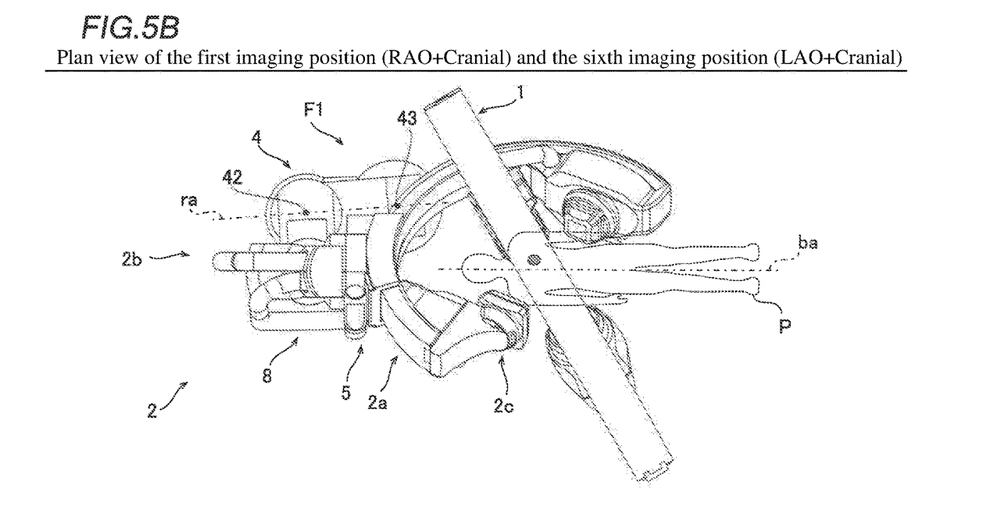
FIG. 5B is a plan view showing the arrangements of the first arm and the second arm at the first imaging position and the sixth imaging position according to one embodiment of the present invention.

FIG. 5 shows an example in which the controller 6 arranges the first arm 1 at the sixth imaging position sp6 and arranges the second arm 2 at the first imaging position sp1 to perform imaging. Specifically, in the example shown in FIG. 5, the controller 6 arranges the first arm 1 at the position in which LAO and Cranial are combined by the first arm driving mechanism 3. Further, the controller 6 arranges the second arm 2 to the position in which RAO and Cranial are combined by the base moving mechanism 4, the second arm driving mechanism 5, and the second base 8. The controller 6 is configured to perform imaging at the first imaging position sp1 and the sixth imaging position sp6 by single imaging (one administering a contrast agent) by using the first arm 1 and the second arm 2.

As shown in FIG. 5A, in this embodiment, the controller 6 is configured to arrange the first arm 1 and the second arm 2 such that the heart Pa of the subject P is arranged at a position where the axis 13 and the axis 23 intersect with each other at each imaging position.

Further, as shown in FIG. 5B, when arranging the first arm 1 and the second arm 2 at the first imaging position sp1 and the sixth imaging position sp6, the dashed line "ra" connecting the base axis 42 and the intermediate axis 43 is approximately oriented in a direction along the body axis "ba" of the subject P. In this embodiment, the arrangement in which the dashed line "ra" and the body axis "ba" of the subject P are oriented approximately parallel to each other is denoted as a first arrangement F1. Note that the body axis "ba" of the subject P denotes an axis that passes through the center of the subject P in short axis direction and extends in the long axis direction of the subject P.

<Imaging at Second Imaging Position and Seventh Imaging Position>

Figure 6A:
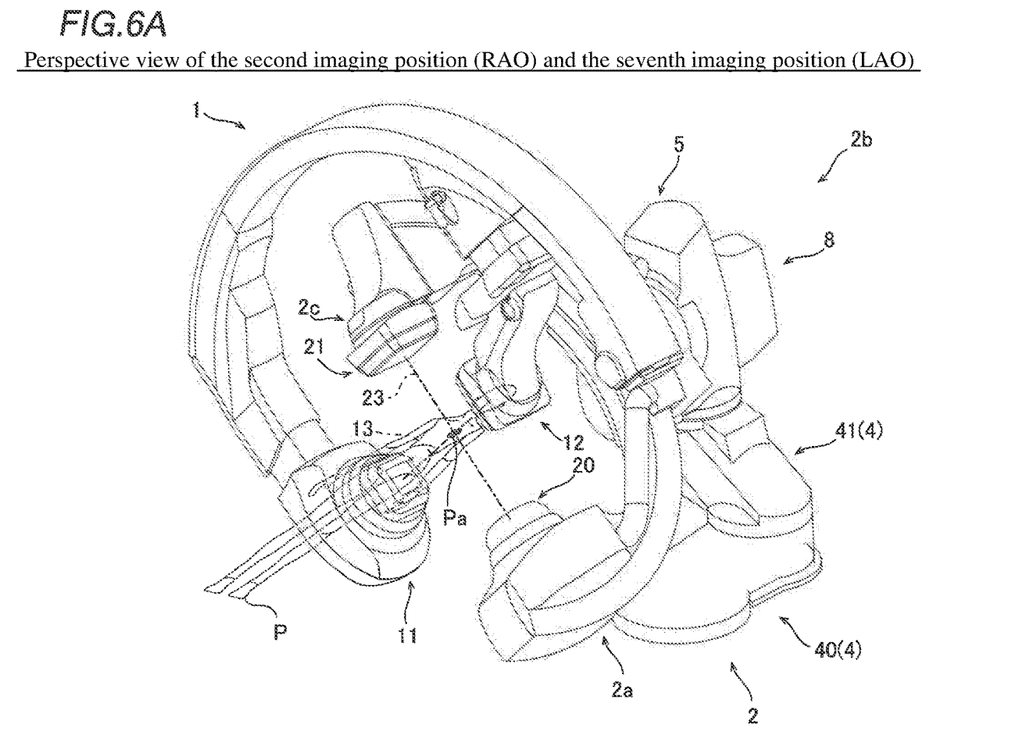
FIG. 6A is a perspective view showing the arrangements of the first arm and the second arm at the second imaging position and the seventh imaging position according to one embodiment of the present invention.
Figure 6B:
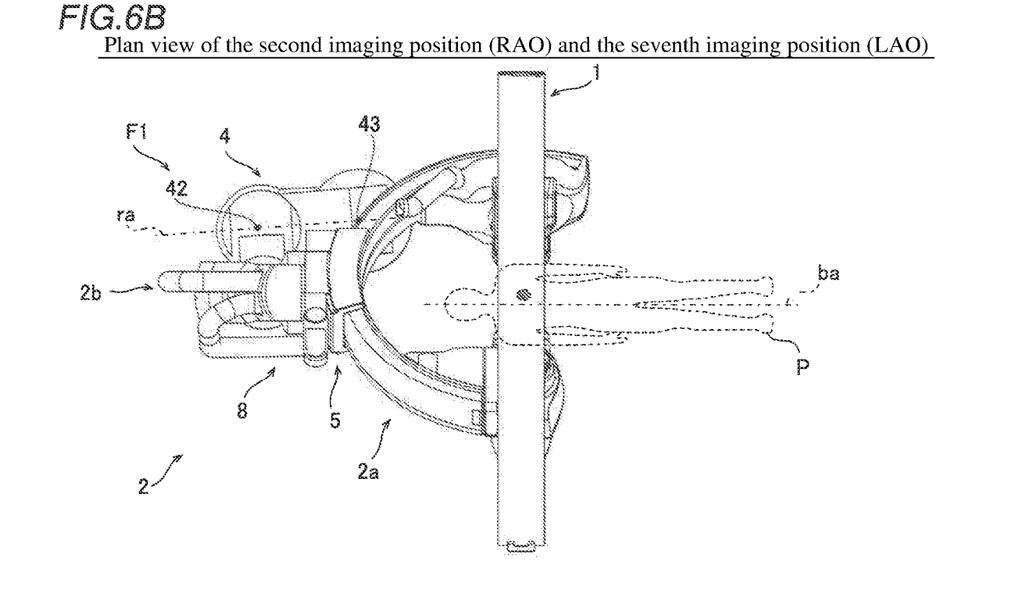
FIG. 6B is a plan view showing the arrangements of the first arm and the second arm at the second imaging position and the seventh imaging position according to one embodiment of the present invention.

FIG. 6 shows an example in which the controller 6 arranges the first arm 1 at the seventh imaging position sp7 and arranges the second arm 2 at the second imaging position sp2 to perform imaging. Specifically, in the embodiment shown in FIG. 6, the controller 6 arranges the first arm 1 at the position of LAO by the first arm driving mechanism 3. Further, the controller 6 arranges the second arm 2 at the position of RAO by the base moving mechanism 4, the second arm driving mechanism 5, and the second base 8. Then, the controller 6 is configured to perform imaging at the second imaging position sp2 and the seventh imaging position sp7 by using the first arm 1 and the second arm 2 by single imaging. Also in the example shown in FIG. 6, the base axis 42 and the intermediate axis 43 are in the first arrangement F1.

<Imaging at Third Imaging Position and Eighth Imaging Position>

Figure 7A:
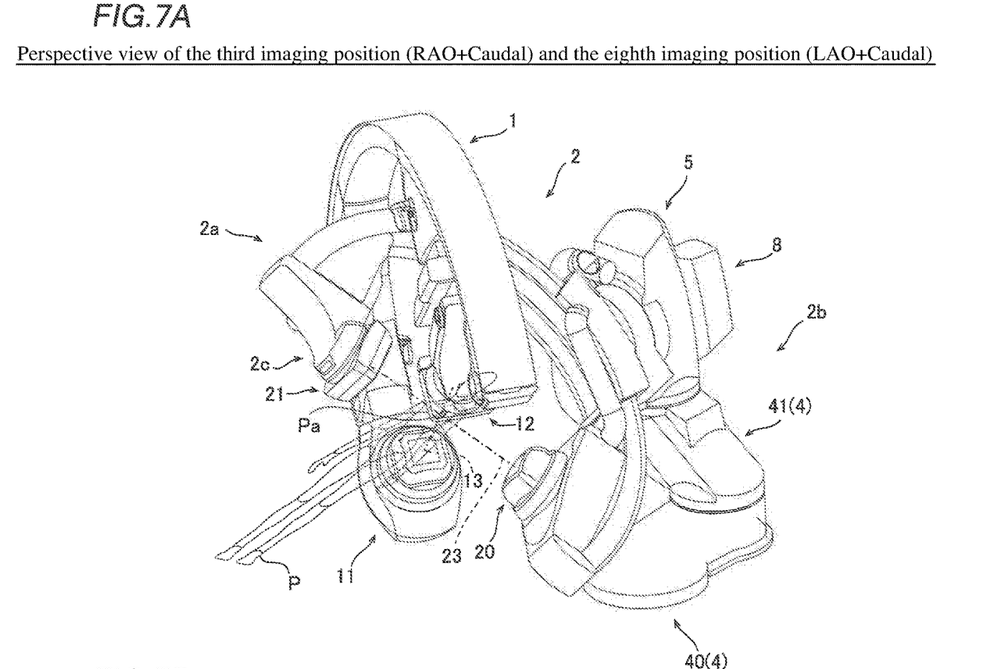
FIG. 7A is a perspective view showing the arrangements of the first arm and the second arm at the third imaging position and the eighth imaging position according to one embodiment of the present invention.
Figure 7B:
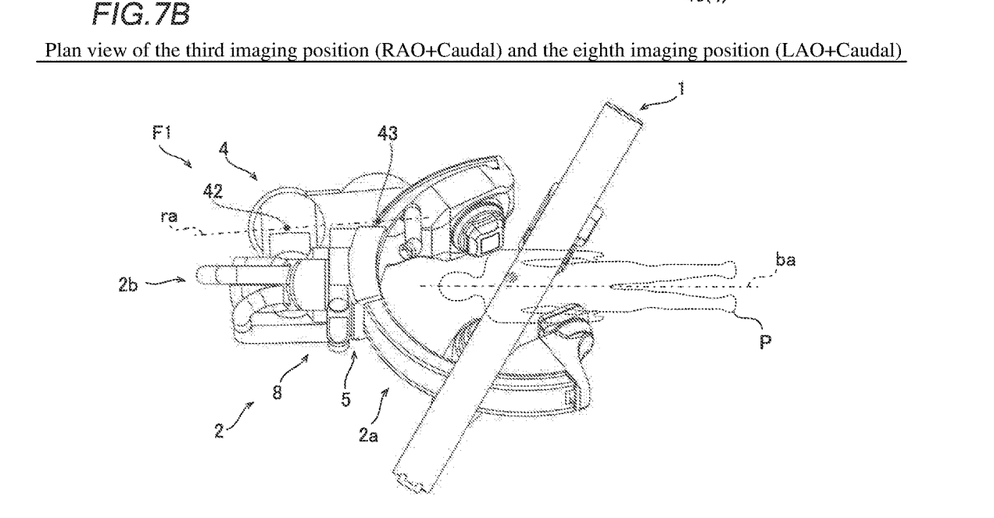
FIG. 7B is a plan view showing the arrangements of the first arm and the second arm at the third imaging position and the eighth imaging position according to one embodiment of the present invention.

FIG. 7 shows an example in which the controller 6 arranges the first arm 1 at the eighth imaging position sp8 and arranges the second arm 2 at the third imaging position sp3. Specifically, in the example shown in FIG. 7, the controller 6 arranges the first arm 1 at a position in which LAO and Caudal are combined by the first arm driving mechanism 3. Also, the controller 6 arranges the second arm 2 at a position in which RAO and Caudal are combined by the base moving mechanism 4, the second arm driving mechanism 5, and the second base 8. Then, the controller 6 is configured to perform imaging by using the first arm 1 and the second arm 2 at the third imaging position sp3 and the eighth imaging position sp8 by single imaging. Also in the example shown in FIG. 7, the base axis 42 and the intermediate axis 43 are in the first arrangement F1.

As shown in FIG. 5B, FIG. 6B, and FIG. 7B, the first arm 1 and the second base 8 arm do not interfere in the combination of the first imaging position sp1 and the sixth imaging position sp6, in the combination of the second imaging position sp2 and the seventh imaging position sp7, and in the combination of the third imaging position sp3 and the eighth imaging position sp8. Therefore, in the arrangements shown in FIG. 5B, FIG. 6B, and FIG. 7B, it is possible to perform imaging at once by using the first arm 1 and the second arm 2 from the respective positions without moving the second base 8.

<Imaging at Fourth Imaging Position and Fifth Imaging Position>

Figure 8:
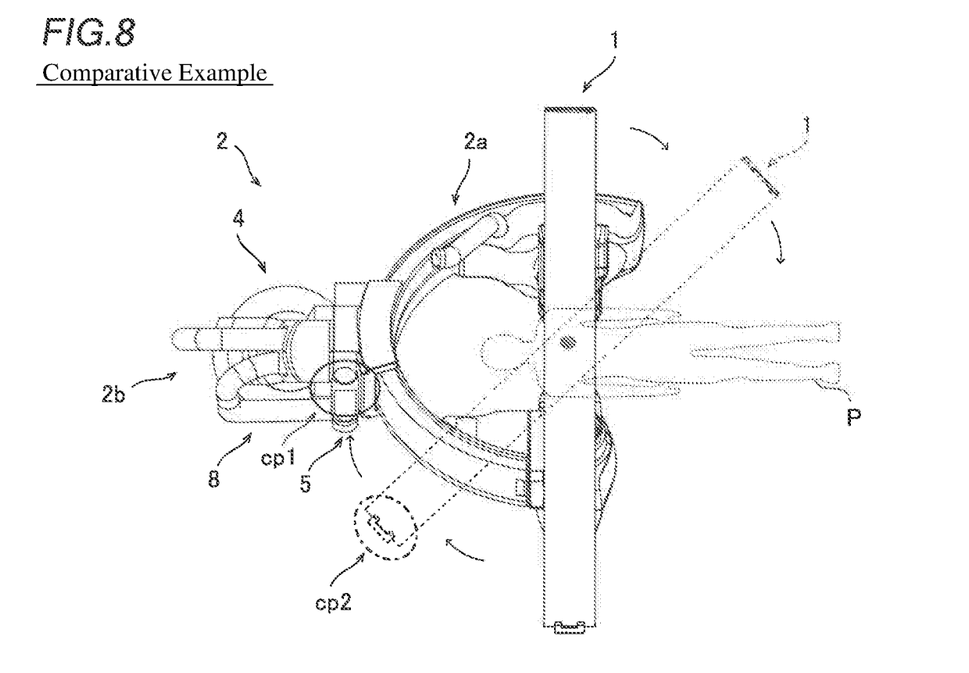
FIG. 8 is a schematic diagram for explaining that the first arm and the second arm cannot be arranged at the fourth imaging position and the fifth imaging position in Comparative Example.

FIG. 8 is a schematic diagram showing an example in which the first arm 1 and the second arm 2 are arranged at the fourth imaging position sp4 and the fifth imaging position sp5 in Comparative Example. FIG. 8 shows an exemplary configuration in which only the base axis 42 is provided in the base moving mechanism 4 and the second base 8 is allowed to rotate only about the base axis 42.

In the configuration of Comparative Example shown in FIG. 8, when it is attempted to arrange the first arm 1 at the fourth imaging position sp4 or the fifth imaging position sp5, since there exists the second base 8 within the rotational trajectory of the first arm 1, when the first arm 1 is attempted to be arranged at the fourth imaging position sp4 or the fifth imaging position sp5, the region cp1 of the second base 8 and the region cp2 of the first arm 1 interfere with each other. Therefore, in the configuration of Comparative Example as shown in FIG. 8, it is not possible to perform imaging at the fourth imaging position sp4 and the fifth imaging position sp5 at a time by using the first arm 1 and the second arm 2.

Therefore, in this embodiment, the controller 6 is configured to move the second base 8 by the base moving mechanism 4 when the first arm 1 and the second arm 2 are moved at respective predetermined imaging angles or when the first arm 1 and the second arm 2 interfere with each other when they have reached predetermined imaging angles. Specifically, when performing imaging at the fourth imaging position sp4 and the fifth imaging position sp5, the controller 6 moves the second base 8 by the base moving mechanism 4 so that the second arm 2 is moved together with the second base 8 to a position where the second arm 2 does not interfere with the first arm 1, and also changes the angle of the second arm 2 by the second arm driving mechanism 5 so that the second arm does not interfere with the first arm 1 and the angle of the second arm 2 becomes a predetermined imaging angle, thereby arranging the first arm 1 and the second arm 2 at mutually non-interference positions to perform imaging.

Figure 9A:
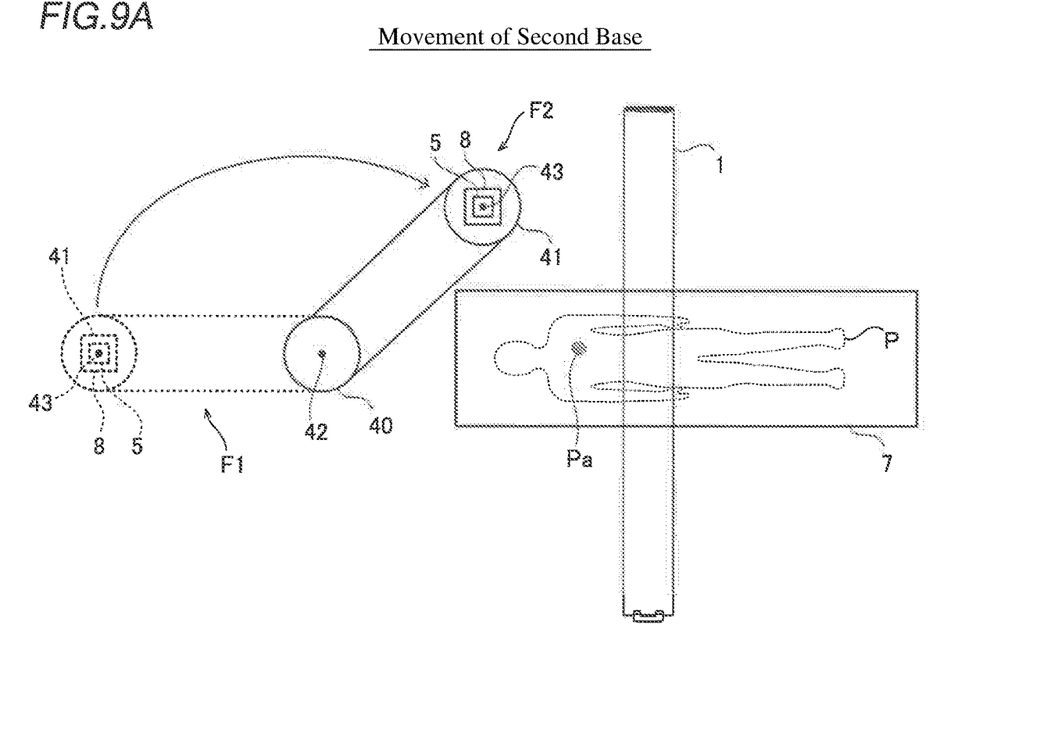
FIG. 9A is a schematic diagram for explaining the processing for arranging the first arm and the second arm at the fourth imaging position and the fifth imaging position according to one embodiment of the present invention.
Figure 9B:
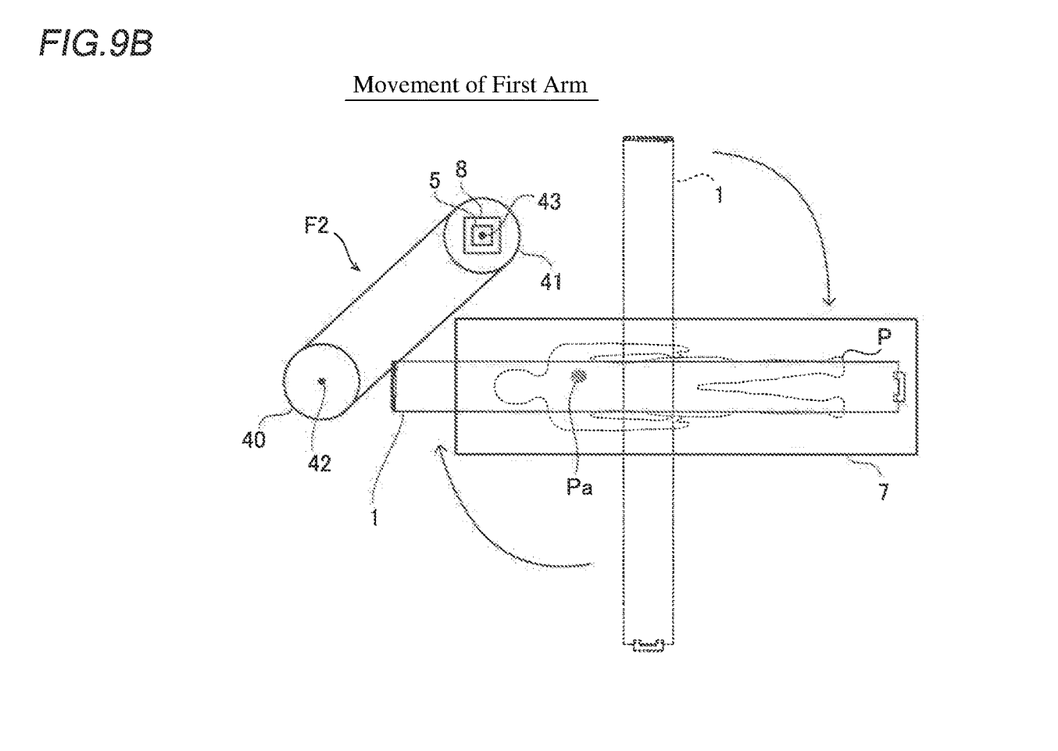
FIG. 9B is a schematic diagram for explaining the processing for arranging the first arm and the second arm at the fourth imaging position and the fifth imaging position according to one embodiment of the present invention.

FIG. 9A shows a schematic diagram when the controller 6 according to this embodiment moves the second base 8 via the base moving mechanism 4. FIG. 9B is a schematic diagram when the controller 6 according to this embodiment moves the first arm 1 via the first arm driving mechanism 3 after moving the second base 8.

As shown in FIG. 9A, the controller 6 is configured to rotate the second base 8 by the base moving mechanism 4 to arrange the intermediate axis 43 on the long side of the top board 7. Specifically, the controller 6 is configured to move the second base 8 from the short side of the top board 7 to the long side of the top board 7 in plan view by the base moving mechanism 4. In the example shown in FIG. 9A, when the top board 7 is viewed from the ceiling side, the controller 6 is configured to move the second base 8 clockwise by the base moving mechanism 4 to move the second base 8. Thus, the dashed line "ra" connecting the base axis 42 and the intermediate axis 43 is oriented in a direction intersecting the body axis "ba" of the subject P. In this embodiment, the arrangement in which the dashed line "ra" and the body axis "ba" of the subject P intersect is denoted as a second arrangement F2. Thereafter, the controller 6 is configured to arrange the first arm 1 on the short side of the top board 7 by the first arm driving mechanism 3, so that the second arm 2 is arranged at a position where the second arm 2 does not interfere with the first arm 1. Note that the long side of the top board 7 denotes a position where the top board 7 and the second base 8 are arranged in the long axis direction of the top board 7. Further note that the short side of the top board 7 denotes a position where the top board 7 and the second base 8 are arranged in the short axis direction of the top board 7.

Figure 10A:
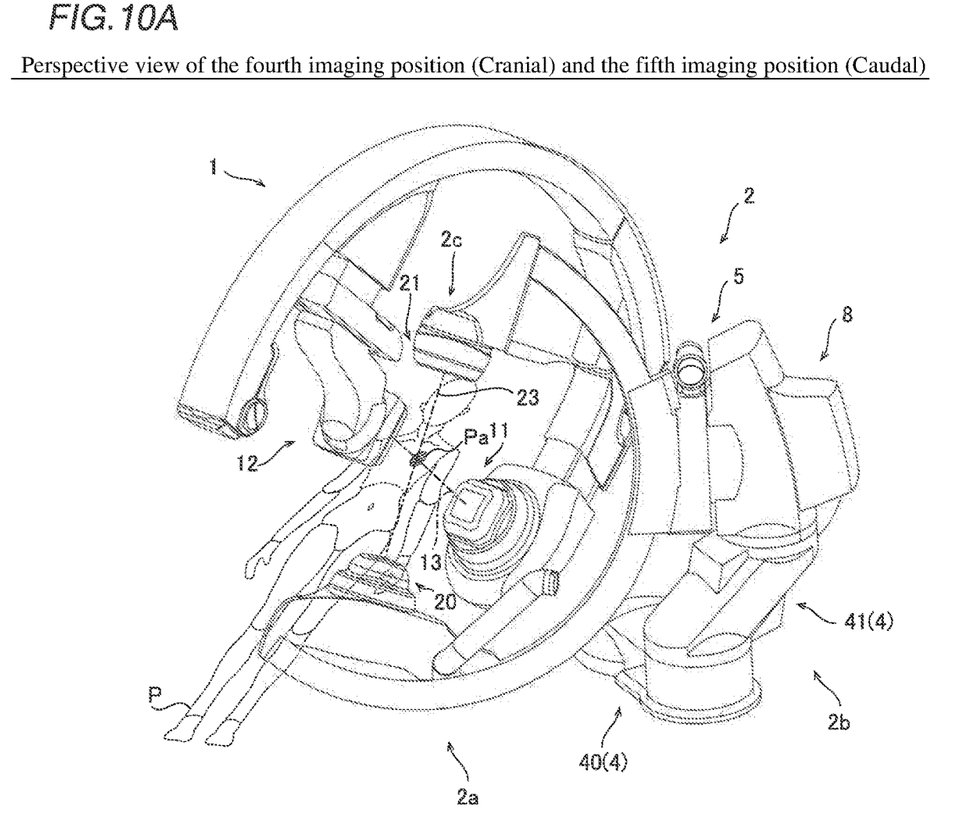
FIG. 10A is a perspective view showing the arrangements of the first arm and the second arm at the fourth imaging position and the fifth imaging position according to one embodiment of the present invention.
Figure 10B:
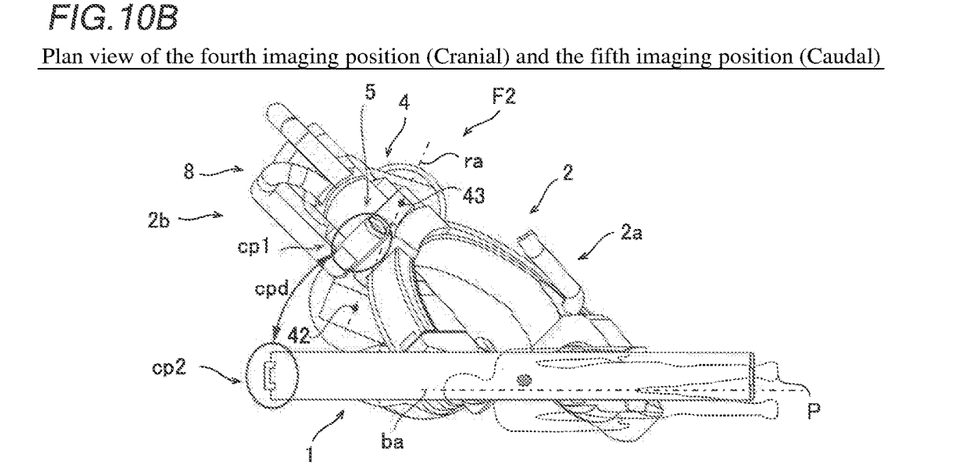
FIG. 10B is a plan view showing the arrangements of the first arm and the second arm at the fourth imaging position and the fifth imaging position according to one embodiment of the present invention.

As shown in FIG. 10, in this embodiment, when imaging at the fourth imaging position sp4 and the fifth imaging position sp5, the controller 6 is configured to arrange the first arm 1 and the second arm 2 at positions (Cranial and Caudal) where X-rays are obliquely emitted to the subject P from one end side and the other end side in the long axis direction of the top board 7 in the longitudinal cross-sectional plane along the long axis of the top board 7 to perform imaging. As shown in FIG. 10, in this embodiment, by arranging the base axis 42 and the intermediate axis 43 at positions in the second arrangement F2, even when the first arm 1 and the second arm 2 are arranged at the fourth imaging position sp4 and the fifth imaging position sp5, respectively, the distance cpd between the region cp2 of the first arm 1 and the region cp1 of the second base 8 becomes large. With this, by using the first arm 1 and the second arm 2, imaging can be performed at the fourth imaging position sp4 and the fifth imaging position sp5 at a time by using the first arm 1 and the second arm 2.

At this time, the controller 6 drives the second arm 2 by the second arm driving mechanism 5 so that the imaging angle at the fourth imaging position sp4 becomes a preset angle. The imaging angle at the fourth imaging position sp4 is an angle in the Cranial direction shown in FIG. 3A.

Further, the controller 6 is configured to rotate the second detector 21 by the detector rotation mechanism 2c by the angle corresponding to the rotation angle of the second arm 2 so that the orientation of the subject P in the X-ray image to be acquired (not shown) does not change due to the rotation of the second arm 2 by the base moving mechanism 4. For example, in the case of FIG. 10, the controller 6 rotates the second detector 21 by the detector rotation mechanism 2c so that the head-foot direction of the subject P is oriented in the up-down direction of the X-ray image.

Imaging Processing at Fourth Imaging Position and Fifth Imaging Position

Figure 11:
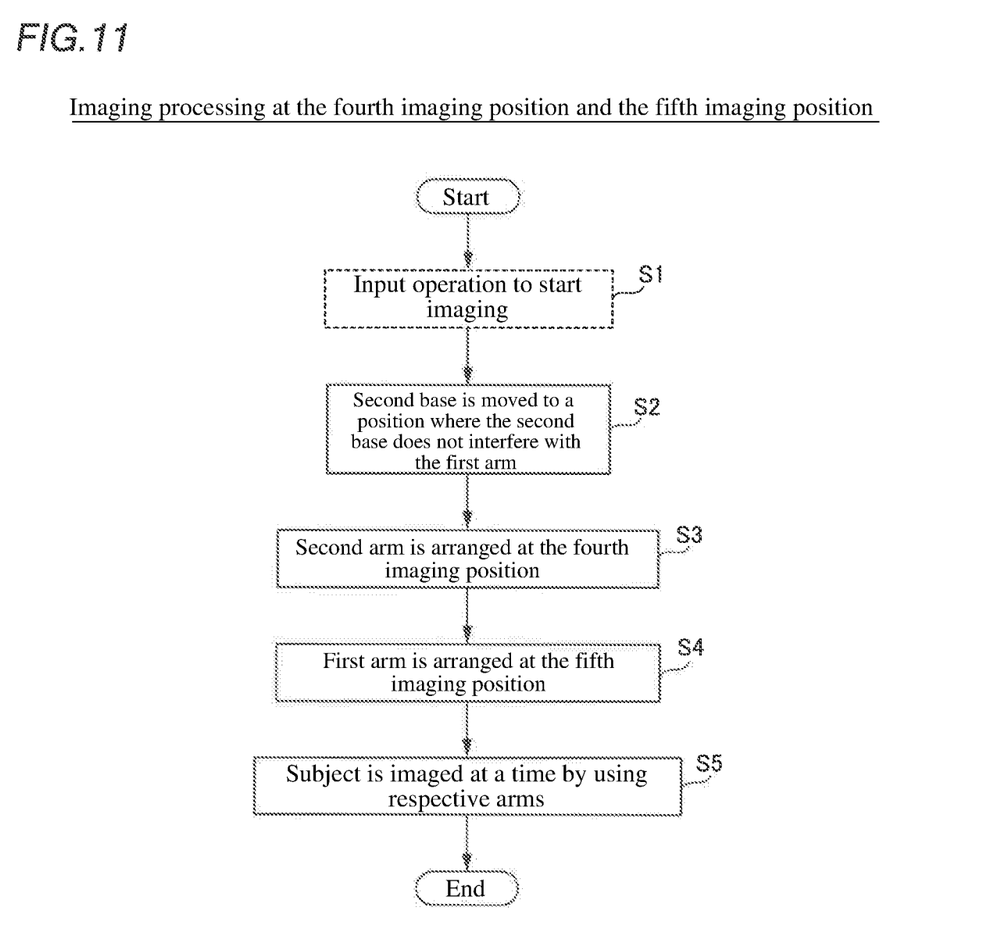
FIG. 11 is a flowchart for explaining the processing of imaging at the fourth imaging position and the fifth imaging position according to one embodiment of the present invention.

Next, referring to FIG. 11, the imaging processing at the fourth imaging position sp4 and the fifth imaging position sp5 in this embodiment will be described.

In Step S1, an input operation to start imaging at the fourth imaging position sp4 and the fifth imaging position sp5 is performed by an operator such as a doctor. Next, in Step S2, the controller 6 moves the second base 8 from the short side of the top board 7 to the long side of the top board 7 by the base moving mechanism 4 to arrange the second arm 2 at a position where the second arm 2 does not interfere with the first arm 1. That is, the controller 6 moves the arrangement of the base axis 42 and the intermediate axis 43 from the position of the first arrangement F1 to the position of the second arrangement F2 by the base moving mechanism 4. Thereafter, the processing proceeds to Step S3.

In Step S3, the controller 6 arranges the second arm 2 at the fourth imaging position sp4 by the second base 8. Thereafter, in Step S4, the controller 6 arranges the first arm 1 at the fifth imaging position sp5 by the first arm driving mechanism 3. Thereafter, the processing proceeds to Step S5.

In Step S5, the controller 6 performs imaging at the fourth imaging position sp4 and the fifth imaging position sp5 at a time by using the first arm 1 and the second arm 2, and ends the processing.

Note that when moving the first arm 1 and the second arm 2 to the respective imaging positions, the controller 6 is configured to move the respective arms to predetermined positions based on the positions stored in advance in the storage unit 10. Further, in cases where the first arm 1 and the second arm 2 are arranged at the respective imaging positions other than the fourth imaging position sp4 and the fifth imaging position sp5, the second base 8 and the first arm 1 do not interfere with each other when the arrangement of the base axis 42 and the intermediate axis 43 is in the first arrangement F1. Therefore, when performing imaging at each imaging position other than the fourth imaging position sp4 and the fifth imaging position sp5, it is enough that the controller 6 is configured to move the arrangement of the base axis 42 and the intermediate axis 43 to the first arrangement F1 in Step S2.

Effects of this Embodiment

In this embodiment, the following effects can be obtained.

In this embodiment, as described above, the X-ray fluoroscopic imaging apparatus 100 includes the first arm 1, the second arm 2, the second arm driving mechanism 5, and the controller 6. The first arm 1 supports the first X-ray source 11 and the first detector 12. The second arm 2 includes the second arm part 2a rotatably held by the second base 8 and configured to support the second X-ray source 20 and the second detector 21 and the base moving mechanism 4 for moving the second base 8. The controller 6 controls the second arm driving mechanism 5 and the base moving mechanism 4. The controller 6 is configured such that in a case where the first arm 1 and the second arm 2 interfere with each other when the first arm 1 and the second arm 2 are moved to respective predetermined imaging angles or when the first arm 1 and the second arm 2 have reached the respective predetermined imaging angles, the second base 8 is moved by the base moving mechanism 4 to move the second arm 2 together with the base unit 2b to a position where the second arm 2 does not interfere with the first arm 1 and that the angle of the second arm 2 is changed by the second arm driving mechanism 5 so that the second arm 2 does not interfere with the first arm 1 and the angle of the second arm 2 becomes the predetermined imaging angle to arrange the first arm 1 and the second arm 2 at imaging positions where the first arm 1 and the second arm 2 do not interfere with each other to perform imaging.

With this, in a case where the first arm 1 and the second arm 2 interfere with each other when the first arm 1 and the second arm 2 are moved to respective predetermined imaging angles or when the first arm 1 and the second arm 2 have reached the respective predetermined imaging angles, it becomes possible to move the second arm 2 together with the base unit 2b, so that the interference between the first arm 1 and the second arm 2 can be prevented. Therefore, even in the case of performing imaging from directions in which the first arm 1 and the second arm 2 interfere with each other, it is possible to perform imaging at a time by using the first arm 1 and the second arm 2. As a result, by administering a contrast agent once, imaging can be performed from two directions in which the first arm 1 and the second arm 2 interfere with each other in single imaging. Therefore, as compared with the case in which the imaging from the directions in which the first arm 1 and the second arm 2 interfere with each other is performed separately in two times, it is possible to suppress the increase in the number of times of administering a contrast agent. It is also possible, for example, to perform imaging from Cranial and Caudal at one time. As a consequence, as compared with the case in which imaging is performed separately from Cranial and Caudal, the number of times of imaging can be reduced and the imaging time can be shortened. As described above, in this embodiment, the X-ray fluoroscopic imaging apparatus 100 can suppress the increase in the number of times of administering a contrast agent and also can shorten the imaging time.

Further, in this embodiment, as described above, the base moving mechanism 4 has the base axis 42 provided on the floor FS and the intermediate axis 43 provided at the position away from the base axis 42, and the controller 6 is configured to arrange the second arm 2 in the position where the second arm 2 does not interfere with the first arm 1 by rotating the base unit 2b by the base moving mechanism 4 to rotate the second arm 2. With this, since the base axis 42 and the intermediate axis 43 are provided at positions away from each other, by rotating the base unit 2b, it is possible to easily change the position of the second arm 2. Consequently, by rotating the base unit 2b, it is possible to easily arrange the second arm 2 at a position where the second arm 2 does not interfere with the first arm 1.

Further, in this embodiment, as described above, the base axis 42 and the intermediate axis 43 are each provided in a direction extending in the vertical direction with respect to the floor FS and the controller 6 is configured to rotate the base unit 2b by the base moving mechanism 4 to arrange the intermediate axis 43 on the long side of the top board 7 for placing a subject thereon. With this, it is possible to arrange the intermediate axis 43 on the long side of the top board 7, and therefore when the first arm 1 is moved on the short side of the top board 7, it is possible to suppress that a part of the first arm 1 and the second arm 2 interfere with each other. As a result, it is possible to more assuredly suppress a part of the second arm 2 from interfering with the first arm 1.

Further, in this embodiment, as described above, the second arm 2 further includes the detector rotation mechanism 2c for rotating the second detector 21 and the controller 6 is configured to rotate the second detector 21 by the detector rotation mechanism 2c by the angle corresponding to the rotation angle of the second arm 2 so that the orientation of the subject P in the X-ray image to be acquired does not change due to the rotation of the second arm 2 by the base moving mechanism 4.

With this, by rotating the second detector 21 in response to the rotation angle of the second arm 2, even in cases where the second arm 2 is arranged at a position where the second arm 2 does not interfere with the first arm 1 when imaging the subject P from a desired imaging angle by using the second arm 2, it is possible to acquire the same X-ray image as when imaging without rotating the second arm 2. Therefore, when imaging the subject P from the desired imaging angle, it is possible to perform imaging the subject P so that the orientation of the subject P in the X-ray image is oriented in the desired direction. As a result, the user usability can be improved.

Further, in this embodiment, as described above, the controller 6 is configured to perform imaging by arranging the first arm 1 and the second arm 2 at positions in which X-rays are obliquely emitted to the subject P from one end side and the other end side of the top board 7 in the long axis direction of the top board 7 in the longitudinal cross-sectional plane along the long axis of the top board 7 for placing a subject P thereon. With this, even in the case of imaging a subject P from two different directions on one end side and the other end side of the top board 7 in the long axis direction of the top board 7, it is possible to suppress that the first arm 1 and the second arm 2 interfere with each other. Consequently, imaging from two different directions on one end side and the other end side of the top board 7 in the long axis direction of the top board 7 can be performed by single imaging.

Further, in this embodiment, as described above, the first arm driving mechanism 3 for driving the first arm 1 is further provided, and the controller 6 is configured to arrange the second arm 2 to a position where the second arm 2 does not interfere with the first arm 1 by moving the base unit 2b from the short side of the top board 7 for placing a subject P thereon to the long side of the top board 7 by the base moving mechanism 4 and arranging the first arm 1 on the short side of the top board 7 by the first arm driving mechanism 3.

With this, after moving the base unit 2b from the short side of the top board 7 to the long side of the top board 7, the first arm 1 can be arranged on the short side of the top board 7. Consequently, even in cases where the second arm 2 has been arranged at a position where the second arm 2 interferes with the first arm 1, the first arm 1 can be moved after moving the second arm 2. Therefore, it is possible to assuredly suppress the interference between the second arm 2 and the first arm 1.

Further, in this embodiment, as described above, the controller 6 is configured to perform imaging from eight directions in which the left-right direction in the horizontal plane along the long axis of the top board 7 for placing a subject P thereon and directions in which X-rays are obliquely emitted to the subject P from one end side or the other end side of the top board 7 in the longitudinal cross-sectional plane along the long axis of the top board 7 are combined by arranging the first arm 1 and second arm 2 at mutually different four relative positions.

With this, imaging from eight directions can be performed by arranging the first arm 1 and the second arm 2 at four relative positions. As a result, as compared with the case in which imaging is performed separately from the directions in which X-rays are obliquely emitted to the subject P from one end side or the other end side of the top board 7 in the longitudinal cross-sectional plane along the long axis of the top board 7, the number of times of imaging can be reduced, which in turn can suppress the increase in the number of times of administering a contrast agent.

Further, in this embodiment, as described above, the X-ray fluoroscopy apparatus 100 is provided with the imaging unit 9 and the controller 6. The imaging unit 9 includes the first arm 1 and the second arm 2 and can image the subject P from different directions. The controller 6 controls the imaging unit 9. The controller 6 is configured to perform imaging from eight directions in which each of a right oblique direction, a front direction, and a left oblique direction of the subject P and directions in which X-rays are obliquely emitted to the subject P from one end side or the other side of the top board 7 for placing the subject P thereon in a longitudinal cross-sectional plane along the long axis of the top board 7 are combined. In a case in which the first arm 1 and the second arm 2 interfere with each other when the first arm 1 and the second arm 2 are moved to respective predetermined imaging angles or when the first arm 1 and the second arm 2 have reached the respective predetermined imaging angles at a time of imaging the subject P from directions in which a direction facing a front of the subject P and directions in which X-rays are obliquely emitted to the subject from one end side or the other end side of the top board 7 in the longitudinal cross-sectional plane along the long axis of the top board 7 for placing the subject thereon are combined, between the eight directions, the controller 8 arranges the first arm 1 and the second arm 2 at mutually non-interference positions to image the subject by rotating the base unit 2*b* of the second arm 2 to rotate the second arm 2 together with the base unit 2*b* and changes the angle of the second arm 2 so that the second arm 2 does not interfere with the first arm 1 and the angle of the second arm 2 becomes a predetermined imaging angle.

With this, it is possible to perform imaging at a time from two directions in which the first arm 1 and the second arm 2 interfere with each other by using the first arm 1 and the second arm 2. Therefore, by imaging four times in two directions, imaging in eight directions can be performed, so that it is possible to suppress the increase in the number of times of administering a contrast agent. Further, by performing imaging four times in each of two directions, it is possible to perform imaging in eight directions. Therefore, the number of times of imaging can be reduced, which in turn can shorten the imaging time. As described above, in this embodiment, it is possible to provide an X-ray fluoroscopic imaging apparatus 100 capable of suppressing the number of times of administering a contrast agent and shortening the imaging time.

Modifications

It should be understood that the embodiments disclosed here are examples in all respects and are not restrictive. The scope of the present invention is shown in the claims rather than by the aforementioned embodiments, and the scope of the present invention includes all modifications (modified examples) within the meanings and ranges equivalent to the claims.

For example, in the above-described embodiment, an example is shown in which the first arm 1 is held from the ceiling CS, but the present invention is not limited thereto. For example, in the same manner as in the second arm 2, the first arm 1 may be configured to be held by a base moving mechanism provided on the floor FS.

In the above-described embodiment, an example is shown in which the first detector 12 and the second detector 21 are arranged on the front side of the top board (the side on which a subject P is placed), but the present invention is not limited thereto. For example, the first X-ray source 11 and the second X-ray source 20 may be arranged on the front side of the top board 7.

In the above-described embodiment, an example is shown in which the base moving mechanism 4 has the base axis 42, the intermediate axis 43, and the horizontal rotation axis 44, but the present invention is not limited thereto. For example, the base moving mechanism 4 may be configured to have two axes of the base axis 42 and the intermediate axis 43. However, the more the number of rotation axes the base moving mechanism 4 has, the degree of freedom in the movement of the base unit 2*b* and the second arm 2 improves. Therefore, the base moving mechanism 4 is preferably configured to include the base axis 42, the intermediate axis 43, and the horizontal rotation axis 44.

Further, in the explanatory embodiment shown in FIG. 9, an example is shown in which the base moving mechanism 4 rotates the second base 8 clockwise to move the second base 8 when the top board 7 is viewed from the ceiling side, but the present invention is not limited thereto. The base moving mechanism 4 may be configured to rotate the second base 8 counterclockwise when the top board 7 is viewed from the ceiling.

In the above-described embodiment, an example is shown in which the base moving mechanism 4 is arranged at a position in which the base moving mechanism 4 and the top board 7 are aligned along the long axis of the top board 7, but the present invention is not limited thereto. For example, the base moving mechanism 4 may be arranged at a position displaced from the long axis direction of the top board 7 to either the left or right from the direction along the long axis of the top board 7. When arranging the base moving mechanism 4 at a position shifted from the long axis of the top board 7 to the left, the base moving mechanism 4 may be configured to rotate the second base 8 counterclockwise when the top board 7 is viewed from the ceiling side. Further, when arranging the base moving mechanism 4 at a position shifted from the long axis direction of the top board 7 to the right, it is sufficient to configure such that the base 8 is rotated clockwise when the top board 7 is viewed from the ceiling side.

The invention claimed is:

1. An X-ray fluoroscopic imaging apparatus comprising:
   a first arm configured to support a first X-ray source and a first detector;
   a second arm including a second arm part and a base unit, the second arm part being held by a base and configured to support a second X-ray source and a second detector, and the base unit including a base moving mechanism for moving the base;
   a second arm driving mechanism configured to drive the second arm; and
   a controller configured to control the second arm driving mechanism and the base moving mechanism, wherein the controller is configured such that in a case where the first arm and the second arm interfere with each other when the first arm and the second arm are moved to respective predetermined imaging angles or when the first arm and the second arm have reached the respective predetermined imaging angles, the base is moved by the base moving mechanism to move the second arm together with the base unit to a position where the second arm does not interfere with the first arm and that an angle of the second arm is changed by the second arm driving mechanism so that the second arm does not interfere with the first arm and the angle of the second arm becomes the predetermined imaging angle to arrange the first arm and the second arm at positions where the first arm and the second arm do not interfere with each other to perform imaging.

2. The X-ray fluoroscopic imaging apparatus as recited in claim 1,
wherein the base moving mechanism includes a first rotation axis provided on a floor and a second rotation axis provided at a position away from the first rotation axis, and
wherein the controller is configured to rotate the base unit by the base moving mechanism to rotate the second arm so that the second arm is arranged at a position where the second arm does not interfere with the first arm.

3. The X-ray fluoroscopic imaging apparatus as recited in claim 2,
wherein the first rotation axis and the second rotation axis are each a rotation axis oriented in a vertical direction with respect to the floor, and
wherein the controller is configured to rotate the base unit by the base moving mechanism to arrange the second rotation axis on a long side of a top board for placing a subject thereon.

4. The X-ray fluoroscopic imaging apparatus as recited in claim 2,
wherein the second arm further includes a detector rotation mechanism for rotating the second detector, and
wherein the controller is configured to rotate the second detector by the detector rotation mechanism by an angle corresponding to a rotation angle of the second arm so as not to change an orientation of a subject in an X-ray image to be acquired due to rotation of the second arm by the base moving mechanism.

5. The X-ray fluoroscopic imaging apparatus as recited in claim 1,
wherein the controller is configured to arrange the first arm and the second arm at positions where X-rays are emitted to the subject in oblique directions from one end side and the other end side of the top board in a longitudinal cross-sectional plane along a long axis of the top board to perform imaging.

6. The X-ray fluoroscopic imaging apparatus as recited in claim 1, further comprising:
a first arm driving mechanism configured to drive the first arm,
wherein the controller is configured to move the base unit by the base moving mechanism from a short side of the top board for placing a subject thereon to a long side thereof in a plan view and arrange the first arm by the first arm driving mechanism on the short side of the top board so that the second arm is arranged at a position where the second arm does not interfere with the first arm.

7. The X-ray fluoroscopic imaging apparatus as recited in claim 1,
wherein the controller is configured to arrange the first arm and the second arm at mutually different four relative positions to image a subject from eight directions in which a short axis direction of the top board in a horizontal plane along a long axis of the top board for placing a subject thereon and directions in which X-rays are obliquely emitted to a subject from one end side or the other end side of the top board in a longitudinal cross-sectional plane along the long axis of the top board are combined.

8. An X-ray fluoroscopic imaging apparatus comprising:
an imaging unit including a first arm and a second arm, the imaging unit being capable of imaging a subject from different directions; and
a controller configured to control the imaging unit,
wherein the controller is configured to perform imaging from eight directions in which each of a right oblique direction, a front direction, and a left oblique direction of the subject and directions in which X-rays are obliquely emitted to the subject from one end side or the other end side of a top board for placing a subject thereon in a longitudinal cross-sectional plane along a long axis of the top board are combined, and
wherein in a case in which the first arm and the second arm interfere with each other when the first arm and the second arm are moved to respective predetermined imaging angles or when the first arm and the second arm have reached the respective predetermined imaging angles at a time of imaging the subject in directions in which the front direction of the subject and directions in which X-rays are emitted to the subject from one end side or the other end side of the top board are combined, between eight directions,
the controller is configured to rotate a base unit of the second arm to rotate the second arm together with the base unit and change an angle of the second arm so that the second arm does not interfere with the first arm and the angle of the second arm becomes a predetermined imaging angle to arrange the first arm and the second arm at mutually non-interference positions to perform imaging.

* * * * *